United States Patent
Caspar et al.

(10) Patent No.: US 8,706,425 B2
(45) Date of Patent: Apr. 22, 2014

(54) METHOD FOR VALIDATION OF POLYMER AQUEOUS SOLUTIONS CONCENTRATION AND ACTIVATION IN WATER TREATMENT APPLICATIONS AND POLYMER MAKE-UP UNIT THEREFOR

(75) Inventors: Martin Caspar, Montreal (CA); Marianne Dupla, Montreal (CA); Philippe Lacroix, Lachine (CA); Josee Lalonde, Mascouche (CA); Hugo Sabourin, Deux Montagnes (CA)

(73) Assignee: Veolia Water Solutions & Technologies Support, Saint Maurice (FR)

( * ) Notice: Subject to any disclaimer, the term of this patent is extended or adjusted under 35 U.S.C. 154(b) by 326 days.

(21) Appl. No.: 13/186,722

(22) Filed: Jul. 20, 2011

(65) Prior Publication Data

US 2013/0024132 A1   Jan. 24, 2013

(51) Int. Cl.
*G06F 19/00* (2011.01)
*G01N 15/06* (2006.01)

(52) U.S. Cl.
CPC ................................. *G01N 15/06* (2013.01)
USPC .......................................................... 702/25

(58) Field of Classification Search
CPC .................................................... G01N 15/06
USPC .................................................... 702/25, 85
See application file for complete search history.

(56) References Cited

U.S. PATENT DOCUMENTS

| 4,024,883 | A | 5/1977 | Akgungor et al. |
| 5,750,614 | A | 5/1998 | Hund et al. |
| 6,750,328 | B1 | 6/2004 | Wetegrove et al. |
| 7,532,321 | B2 | 5/2009 | Stave et al. |
| 2009/0017548 | A1 * | 1/2009 | Ratcliff et al. ................ 436/124 |
| 2010/0096335 | A1 | 4/2010 | Sauvignet et al. |

FOREIGN PATENT DOCUMENTS

| EP | 0467219 A2 | 1/1992 |
| FR | 2390983 A1 | 12/1978 |
| JP | 59166216 A | 9/1984 |
| WO | 9604398 A1 | 2/1996 |
| WO | 0010007 A2 | 2/2000 |
| WO | 2009121728 A2 | 10/2009 |

* cited by examiner

*Primary Examiner* — Bryan Bui
(74) *Attorney, Agent, or Firm* — Fraser Clemens Martin & Miller LLC; J. Douglas Miller

(57) ABSTRACT

The method of quantifying and of validation of activation status of a water treatment polymer in an aqueous sample includes the following steps: supplying polymer, e.g. continuously, to the aqueous sample; monitoring electrical conductivity measurements in the aqueous sample; thoroughly mixing the aqueous sample; correlating the conductivity measurements with the polymer concentration and activation status; and suspending mixing once conductivity steady state is achieved upon the aqueous solution polymer becoming fully activated.

17 Claims, 16 Drawing Sheets

METHOD FOR VALIDATION OF POLYMER AQUEOUS SOLUTIONS CONCENTRATION AND ACTIVATION IN WATER TREATMENT APPLICATIONS AND POLYMER MAKE-UP UNIT THEREFOR

BACKGROUND OF THE INVENTION

Polymers are widely used for different water treatment applications such as flocculation, decantation, sludge thickening and conditioning and many others. Polymers, when properly activated (after the polymerisation phase) have the ability to develop ionic charges (positive or negative) and attract solids present in the different above-noted process. This reaction is commonly known as flocculation. Polymers are usually supplied as dry or liquid forms and are diluted to a certain concentration based upon available process equipment, to be used in the flocculation processes.

A problem with available systems used for diluting dry polymer, is that they do not actually offer a proven and cost effective method to validate polymer make-up concentration or polymer activation status. Therefore, during water treatment site visits and start-ups, many plant operators complain about their inability to obtain adequate information to validate quality and concentration or produced polymer solution.

A polymer is composed of many monomer units joined together via a chemical reaction called polymerization, or "activation of polymer". The degree of polymerization is the number of monomer units in the chain. The chain can be very long—this tremendous length gives polymers some of their unique properties. The molecular weight of a polymer is the degree of polymerization multiplied by the molecular weight of the monomer unit. Acrylmide monomer has a molecular weight of 71. A polymer molecule with a degree of polymerization of 100,000 is made up of 100,000 acrylmide monomer units and will have a molecular weight of 7.1 million (100,000×71).

Organic or synthetic polymers (or polyelectrolytes) are essentially water soluble linear polymers with molecular weights as low as a few hundred thousand and as high as ten million or greater. These products are characterized by the existence of ionized (electrically charged) site groups on the polymer molecule. The electrical charge on the polymer molecule can be negative (anionic), positive (cationic) or no charge (non-ionic).

To optimize a dry polymer's performance, it is important to effectively wet each individual particle of polymer. To accomplish this task requires that the polymer be dispersed prior to being introduced into water. Systems which merely meter polymer into a bowl of stagnant water fail to meet this first criteria, and polymer gelling occurs and additional extended mixing and aging is generally required. Reaching optimum polymer performance is difficult, if not impossible, after polymer gelling occurs. In preparing the proper water treatment polymer solution concentration, industry standard is between a 0.25% to 0.6% solution concentration. Preparing a solution concentration in excess of this can result in increased viscosities and more difficult handling of polymer solution. As viscosity increases, so does the aging time required to reach optimum polymer performance. Note that initial make-down solution concentration often is different than final feed concentration. Final feed concentration can be as low as 0.1%. To achieve final solution concentration, a post dilution system is provided downstream of the solution metering pump.

Standard recommended minimum aging is 30 minutes for simple to hydrate polymers. As a general rule, though, and for design purposes, a minimum of 45 to 90 minutes is recommended when preparing solution concentration of up to 0.5%. Anionic polymers (negatively charged) can be more difficult to hydrate than cationic polymers (positively charged). The general "rule of thumb" (an approximate value based on guess work) of anionic polymers is to double the aging time. The amount of mixing time strongly depends on the polymer being used and the water temperature (temperature below 10 to −15 degrees Celsius will requires additional mixing time). Simple to hydrate polymers should be mixed only long enough to prevent the polymer particles from settling out. These particles will not settle out after they have hydrated to the point where they cannot be seen. For more difficult polymers, longer mixing may be required. Over mixing will damage the polymer and reduce the polymer's effectiveness.

Polymers (ionic type) will increase conductance of water and this effect can be measured with a conductivity meter. Conductance variation is affected by the concentration of the ions and by the nature of polymers used. Conductivity variation is different for strong and weak electrolytes.

Also, viscosity increase can be correlated to polymer chain formation and activation process.

In Japanese patent application No JP 59166216 published Sep. 19, 1984 to the Japanese company Kubota for a "method for controlling supply of flocculant in waste water treatment", waste water is aerated, and the electric conductivity of the water is measured before supplying the flocculant. Accordingly with this conductivity, the supplying amount of flocculant can be controlled. Into a re-aerating tank to be re-aerated, a polymer is supplied as a flocculant through a control mechanism at solid-liquid separation precipitation tank. In order to configure the control mechanism, the electric conductivity of the threaded water from the re-aeration tank is measured by a measuring device before adding the flocculant, the signal from the measuring device is supplied to a control panel and its signal pressure on measured electric conductivity degree is used for input to a flow rate control valve and to be connected to a polymer tank, as well as to control valves. While controlling in proportion to the increase and decrease of the electric conductivity of the treated water, the amount of polymer is also controlled.

This Kubota patent therefore consists of a method to control the addition of flocculant in a waste water treatment chain. The current technologies do not readily allow the control of flocculant addition to assist in solid/liquid separation. A measure of conductivity is taken in the waste water in the presence of chlorine ions before addition of flocculants. The introduction of flocculants produce a variation in the electrical conductivity and this variation enables addition of required chemical products (polymer+aluminum sulphate).

However, the Kubota method is used for control of the quantity of chemical products supplied to a waste water treatment method, by measuring the variation of conductivity produced by addition of several reacting agents with one another. Such a method cannot be readily used in industry, since the polymers and the coagulants (such as aluminum sulphate) are not prepared or used together and are not necessarily controlled by the same parameters.

In U.S. Pat. No. 7,532,321 issued May 12, 2009 to Strategic Diagnostics Inc. for "compositions and methods for the detection of water treatment polymers" ('321 patent), there is disclosed that water soluble polymers play a role in coagulation and flocculation for waste water and drinking water clarification. In aqueous systems, the level of active polymer is not simply a function of how much polymer has been added. Because polymers generally add cost to processes employing them, it is desirable to be able to use them efficiently. There is further disclosed in the '321 patent that polyacrylic acid-based polymers are used as water treatment polymers, such as for the treatment of industrial cooling water to prevent corrosion and mineral deposits, or scale.

Generally, active water treatment polymers remove dissolved minerals from cooling water by complexing with the minerals. Over time, the complexation sites of the water treatment polymer molecules become saturated. The polymer molecules then become "bound" or inactive and are unable to remove any additional minerals from the cooling water. To prevent corrosion and scale damage to machinery, as the water treatment polymers are inactivated they must be removed and replaced by active polymers. Thus, active polymers must be continually fed into the cooling water to replace the inactive polymers. Maintaining the proper feed level for the active polymers is essential for optimum performance of the cooling water system. An improper feed rate can lead to serious problems. For example, an insufficient amount of active polymer can result in the water treatment being overwhelmed by dissolved minerals, thereby causing severe corrosion or scale deposit. On the other hand, maintaining too high a level of the active polymer is expensive and results in an inefficient method for treating industrial cooling water.

In the '321 patent, it is recognized that although several methods are available for determining the concentration of polymer in an industrial cooling water system, these techniques are unsatisfactory because they only determine the concentration of total polymer, i.e., active plus inactive polymer, and do not provide information regarding the concentration of active polymer alone. Moreover, available methods suffer from a lack of specificity and/or sensitivity.

Existing tests detect any polyanionic material and do not distinguish between active and inactive polymer concentrations. In addition, these methods have a detection threshold of only about 50 ppm polymer. Therefore, the total amount of active sulfonated polymer in an industrial cooling water system cannot currently be inexpensively, rapidly or reliably determined. Furthermore, currently available methods collect a sample at a given point in time, thereby providing the operator with only a snap shot rather than a moving picture in a highly dynamic system that is seeing a tremendous amount of change caused by chemical and physical stresses to the treatment polymer.

Still in the '321 patent, there is disclosed that cationic polymers are used in several areas of industrial water treatment such as paper manufacture, effluent stream clarification, sludge dewatering, mineral process and others. When discharged into the environment, excessive amounts of cationic polymers may be problematic. It is therefore desirable to know, with specificity and precision, the amount of residual cationic polymer in a sample prior to discharge. Many currently available methods of determining cationic polymer concentrations in waste water and other water treatment systems suffer from a lack of specificity or sensitivity as with the sulfonated copolymer detection methods described above.

However, the '321 patent utilizes Raman spectroscopy to detect the presence or amount of water treatment polymer either directly or indirectly. The water treatment polymer to be detected can be either an active water treatment polymer or an inactive water treatment polymer.

Although water treatment polymers themselves are generally not detectable by Raman spectroscopy, the polymers may be modified in such a way that they include a chemical moiety that is detectable or the polymers can be combined with a tracer molecule that is detectable.

The water treatment polymer can be modified or designed to contain one or more functional groups that are detectable by Raman spectroscopy at a different frequency when in a non-complexed (active) and/or complexed (inactive) state. This allows the absolute amounts of total polymer, or alternatively, the relative amounts of active and/or inactive water treatment polymer to be calculated. The total amount of polymer can be calculated by using different levels of the active and inactive states and making a calibration curve. The relative amounts of the active and inactive states can then be ascertained by comparing the measured value to the calibration curve. Alternatively, the tracer can be used to quantitate the relative amounts of active and/or inactive water treatment polymer. A tracer can be chosen that does not bind to the water treatment polymer if the water treatment polymer is inactive. The tracer resonates in a Raman spectra at one frequency when the tracer is bound to the water treatment polymer and at a different frequency when the tracer is not bound to the polymer. Similarly, a tracer is chosen that does not bind to active water treatment polymer. The relative amounts of tracer are then determined by monitoring the appropriate Raman resonant frequencies and the concentration of inactive water treatment polymer in a sample is calculated.

In a variation, one can employ a tracer that is indicative of the initial dosage. In this variation, the tracer does not bind to anything, but is blended into the product at a fixed ratio and thus is indicative of total product added. One can employ another tracer that binds an "active" chemical or is only available when the "active" chemical is available. By testing for the amount of this other tracer, one can deduce the rate and degree of degradation of polymer. Alternatively and/or additionally, it can be used to adjust the dosage of other additives.

In a further variation, relative concentrations of both active and inactive water treatment polymers in a sample are determined using one or more tracers. For example, one tracer is added that binds to both active and inactive water treatment polymer, but is detected by Raman spectroscopy at one wavelength when bound to active polymer and detected at a different wavelength when bound to inactive polymer.

In U.S. Pat. No. 6,750,328 issued Jun. 15, 2004 to Strategic Diagnostics Inc. for "antibodies for detection of water treatment polymers" ('328 patent), reference is made to antibody assays, and more particularly, to monoclonal antibodies and antibody assays for the detection of cationic, anionic and non-ionic water treatment polymers. In this '328 patent, it is recognized that although several methods are available for determining the total concentration of sulfonated copolymer in an industrial cooling water system, i.e., active plus inactive sulfonated copolymer, these techniques are unsatisfactory since they only determine the concentration of total sulfonated copolymer, and do not measure the concentration of the active sulfonated copolymer. Moreover, these methods suffer from lack of specificity or poor sensitivity.

In the '328 patent, it is recognized that cationic polymers are also useful in many areas of industrial water treatment. These areas include sludge dewatering, and many others. Excessive amounts of cationic polymers may cause problems in waters discharged to the environment. It is therefore recognized to be desirable to know with specificity and precision the amount of residual cationic polymer in a sample. Many prior art methods of determining cationic polymer concentrations in waste water and other water treatment systems suffer from lack of specificity or poor sensitivity as with the sulfonated copolymers described above. Monoclonal antibodies distinguish between an "active" and an "inactive" solution of sulfonated copolymer.

SUMMARY OF THE INVENTION

The present invention is directed at offering a simple and cost-effective method to validate polymer concentration and polymer activation based upon conductivity measurement. This method is easily implemented on a polymer make-up system, to provide a complete and integrated solution to provide feedback to operators when concentration would be incorrect or with inadequate polymer activation. This system will allow plant operators to validate polymer concentration, improve performance of the polymer activation process and eventually offer a better control of the treatment process.

Although conductivity variation is different for strong and weak electrolytes, the present invention focuses on the anionic and cationic polyacrylamide type polymers used in water treatment commonly known as weak electrolytes with high molecular weight. For this type of polymer, the polymerisation reaction involves several complex phenomena that can affect the conductivity measurement such as ionic dissociation degree, concentration and macromolecule size. As a result, conductivity measurement can be very hard to correlate to concentration. However, as the concentrations typically used in the water treatment industry are very low (under 0.5% w/w), a linear relation between concentration and conductivity can be expected and test results (lab scale and full scale) performed by the present inventors have been demonstrated. This concept can be related to the Walden's rule. The Walden's rule is a rule which states that the product of the viscosity and the equivalent ionic conductance at infinite dilution in electrolyte solutions, is a constant, independent of the solvent; this rule being only approximately correct. This rule, written in the form convenient for the present invention, provides a relation between conductivity, S, and viscosity, H, of the aqueous solution:

$$S \times H/nKC = \text{constant}$$

where nKC is the electrolyte concentration.

This model does not offer a valid correlation for all cases, however, after several lab tests and iteration and as our concentrations are relatively low and as polymer molecular weights are relatively constant, we have found this correlation to provide valid scientific background to the present invention under certain specific conditions. Although it is known in the industry that viscosity increase can be correlated to polymer chain formation and activation process, in the present invention, since the polymer chain formation generates electrical charge that can be measured, we have unexpectedly discovered a method to correlate that measurement to the actual polymer solution concentration and polymer activation status.

The present invention confirms that:
conductivity measurement is a valid measurement method to obtain an approximate value of the concentration and of the expression of polymer activation status for polymers used as flocculants/coagulants; and
conductivity measurement of an aqueous solution of polymer enables validation of concentration and/or activation process thereof.

Preferably, the present invention will be integrated into a "black box" application type, including conductivity probe, intelligent control panel (known as "CPU" in the present text) and in-situ validation.

In the present invention, no recourse to rule of thumb and approximation. Our technical solution enables to attain a very precise value, for example such polymer in such conditions will need 15 minutes, or 35 minutes, depending on the conditions and environment, to be activated. No more guess work!

The present invention provides water treatment units operators (potable or not) with a method to confirm that the quality or efficiency of poly-acrylamide is optimal for the process. Compared to the Japanese Kubota patent discussed in our above-noted "background of the invention", the present invention operates substantially upstream relatively to the use and/or quantification of the flocculation addition in the process. Moreover, if the polymer is not thoroughly activated, the Kubota method will not enable detection of this problem and will require increase in flocculation supply to compensate flawed activation (which is an oft-occurring problem in water treatment plants). Also, the Kubota conductivity measuring sensor (referenced 8 in the Kubota patent) will only measure the variation of conductivity in the waste water, whereas in the present invention, our method measures and confirms the effective conductivity found in the polymer tanks (and will be placed upstream of or into the tanks 10 and 11 of Kubota patent) and thus allows operational intervention well before a change in process. Finally, the present invention has been developed to provide plant operators and owners with a method for manufacturing and preparation of polyacrylamide being reliable and precise, and may even enable comparison between different polymers.

In particular, the present invention enables not only to identify concentration of polymer in solutions, but also to provide polymer chains activation level (reactivity) and quantification of polymer activation capability. Polymer activation is one of the key factors in the processes of dehydration or decantation. A well operating method relies on the supply of a quantity of completely activated polymers. If the polymer is not activated, the method will not be operational, whatever the quantity supplied (unless very high doses of multiple orders of magnitude is provided, at an uncompetitively high cost).

The present invention is new and unobvious since no known method provides for a fast, simple and portable method to validate that activation of a polymer or flocculant solution has been thoroughly carried out and is ready to be used in the specific field of water treatment. With a simple conductivity apparatus, operators may validate the quality (i.e. activation) of the solution that was produced, and verify its concentration upon completion of activation. Moreover, the present invention may be retro-fitted to existing automated preparation units, in order to control the quality of the preparation and to alert the users if any flawed recipe has been used. The present method could also allow substantial reduction in both the size of automated systems and the supply of polyacrylamide, since the latter will be much more efficient and ready to use much more quickly.

The present invention method not only measures polymer concentration in a solution, but more to the point allows quantification and real time display and visualization of progression and activation of the polymer in the water treatment field. This method has many different uses since it can be used in different water-treatment related plants and industries.

Accordingly, the invention relates to a method of measuring activation status of a polymer solution in a polymer/water aqueous solution and of expressing concentration thereof; the method comprising the following steps: supplying low activation level polymer to the aqueous solution; providing a verification system for polymer activation of said polymer; calibrating said verification system; generating an activation target value associated with the preceding calibration step; monitoring electrical conductivity in the aqueous solution with said verification system; correlating said conductivity against elapsed time with polymer concentration and polymer activation status; mixing said aqueous solution (for example with an impellor agitator or the like) for a period of maturation time sufficient to enable substantially complete activation of the polymer when conductivity achieves steady state and reaches said target value. Preferably also suspending agitation, once conductivity achieves a steady state associated with complete activation of the polymer. Polymer is then completely activated and ready to use in the water treatment process. Calibration of the polymer activation verification system should be performed in situ on the customer's laboratory and operations floor, and according to customer's specific polymer and water parameters.

Preferably, there is further included a last step of display and confirmation of the activation of the aqueous sample polymer, enabling real time monitoring visualization thereof by an operator and confirmation of quality of produced solution.

The water treatment polymer may be selected from the group comprising weak electrolytes with high molecular weight, and in particular from the group comprising anionic and cationic type polymers.

Said step of supplying polymer to water to form an aqueous solution, could be performed in either a continuous fashion or in a batch mode, or in automatic or manual mode.

The invention also relates to a polymer make-up unit comprising: a water tank enclosing an aqueous solution; a feeding system feeding polymer to said water tank; low activation level polymer being continuously supplied and thoroughly mixed in the aqueous solution inside said water tank; a CPU; a conductivity meter probe sensitive to electrical conductivity in the aqueous solution; said conductivity meter probe and CPU being operatively interconnected wherein said CPU continuously monitors conductivity and correlates against elapsed time said conductivity with polymer concentration and activation status; wherein performance of said water treatment unit is optimized.

Said polymer could then be either continuously supplied in the aqueous solution inside said tank, or intermittently supplied.

For example, the invention could relate to a dry polymer make-up system comprising: an automated make-up system (with high-energy pre-wetting module), an integral CPU, a mixing tank enclosing the activation verification sensor mounting kit; activated polymer being continuously mixed in the mixing tank; a conductivity meter probe sensitive to electrical conductivity in the mixing tank; said conductivity meter probe, and conductivity meter probe being operatively interconnected wherein said CPU continuously monitors conductivity and correlates in real time said conductivity (under Walden's rule) with polymer concentration and activation status; a storage tank enclosing the activation verification sensor mounting kit; a conductivity meter probe sensitive to electrical conductivity in the storage tank; said conductivity meter probe, CPU, and conductivity meter probe being operatively interconnected wherein said CPU continuously monitors conductivity and correlates in real time said conductivity (under Walden's rule) with polymer concentration and activation status; said CPU eventually suspending supply of said polymer in the process if conductivity does not reach the associated conductivity level with complete activation of the aqueous sample polymer; wherein performance of the complete water treatment process could be affected.

Preferably, there is further including a display means accessible by an operator of the water treatment unit and operatively connected to said conductivity probe, and CPU, wherein real time visualization by an operator of concentration and expression of activation status of the polymer in the aqueous solution is enabled.

The invention also relates to a method of optimizing polymer make-up performance, comprising the following steps: feeding water to a polymer make-up unit; diluting low activation level polymer into a water tank, wherein a polymer/water solution is formed inside the tank; monitoring electrical conductivity of said solution; correlating said conductivity with polymer concentration and polymer activation status; and once said conductivity achieves a steady state plateau, suspending feeding of said activated polymer.

The invention also relates to a method of optimizing water treatment plant performance, so that efficient activation of polymer solution is achieved, which could reduce plant down-times and turbidity rises due to inefficient polymer activation and could also reduce polymer raw material overconsumption.

Compared to actual methods developed (and not currently applicable to real day to day operation), the invention is a unique method to determine in a simple and cost-effective manner the activation and potential efficiency status of the polymer solution prior to being supplied to the water treatment units. This method presents the following advantages for the end-user:
- very accurate live readings for the plant operators;
- simple to operate, portable, or process conventional conductivity analyser (plug and play);
- very cost effective method (cost of purchase may be as low as several thousands of dollars while polymer consumption can easily range in hundreds of thousands of dollars on a yearly or bi-yearly basis);
- facilitates water treatment plant control and operation by quantifying polymer quality and efficiency for the plant operator.

This method may help the polymer make-up systems designers and engineers to improve the sizing parameters and optimize costs and design of those units. Please see below typical sizing and design criteria scenario:

a) Conventional Sizing Criteria & System Budgetary Cost

Polymer make-up units are usually sized for 0.3% concentration (weight/weight) and 60-90 minutes maturing time to guarantee complete polymer activation. Let's assume that polymer consumption will be 5 kg/hr on a dry basis:

equivalent polymer solution consumption(at 0.3%):5 kg/hr./0.3%=1666 LPH(liters per hour);

minimum tank capacity if minimum acceptable mixing time (without transferring solution) is 60-90 minutes: 1666 Liters (L) (60 minutes)–2500 L (90 minutes); budgetary price for 1666–2500 L tanks make-up systems: 100,000 $ CAD.

b) Invention Based Sizing Criteria & System Budgetary Cost

Let's assume that invention tests showed that polymer activation can be achieved after 25 minutes (which seems realistic with testing results shown in this study).

Polymer make-up units would then be sized for 0.3% conc. (w/w) and 25 minutes maturing time (which would still guarantee complete polymer activation based upon current invention claim). Let's assume that polymer consumption will be 5 kg/hr on a dry basis:

equivalent polymer solution consumption(at 0.3%):5 kg/hr./0.3%=1666 LPH;

minimum tank capacity if minimum acceptable mixing time (without transferring solution) is 25 minutes: 1666 LPH×25/60=694 L;

budgetary price for 694 L tanks make-up systems: 70 000 $ CAD;

The proposed invention may then also be used to reduce make-up systems sizes and capital investment costs.

DETAILED DESCRIPTION OF THE PREFERRED EMBODIMENT OF THE INVENTION

Having reference to FIGS. 1 to 4 of the drawings, two conductivity meters (Hach® HQ40d, & Oakton Acorn® CON 6 Meter were used, as well as four different polymers: HYDREX® 3551 (anionic 110), HYDREX® 3613 (cationic 492), CIBA® LT 225 (cationic) and CIBA® LT27AG (anionic). Water used was tap water at 22 degrees Celsius, and a ten (10) minutes mixing time of polymer aqueous solution.

Polymer and water were mixed in laboratory using a mixing plate. We tried to test different lab scenarios in order to understand the behaviour of the polymer chain formation and to relate the latter to conductivity readings.

The first tests set goal was to demonstrate that there is a relation between polymer concentration and conductivity measurement. The tests curves suggest that polymer conductivity evolution is probably a non-linear relation that involves several different effects, including polyelectrolyte effect, counter ions, and others.

However, as the exact concentration reading is not a critical factor, accuracy not being critical for our process, we can say that the relation between viscosity and concentration can be represented with a roughly linear relation with a margin of fluctuation varying by about 5 to 10%.

Moreover, it is found from analysis of these curves that point distribution over and under the linear approximation appears to be common for all polymers.

Figure 1:
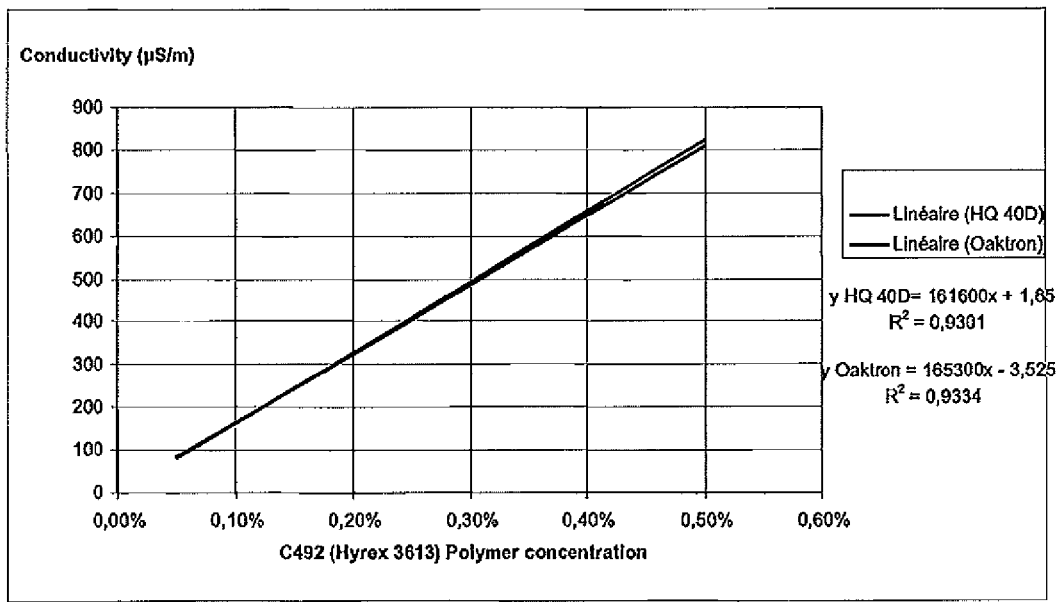
FIGS. 1 to 4 are graphs showing the linear relation between aqueous solution polymer concentration and electrical conductivity measurement of this aqueous solution, for four different polymers, between 0.05 and 0.25% in polymer concentration.
Figure 2:
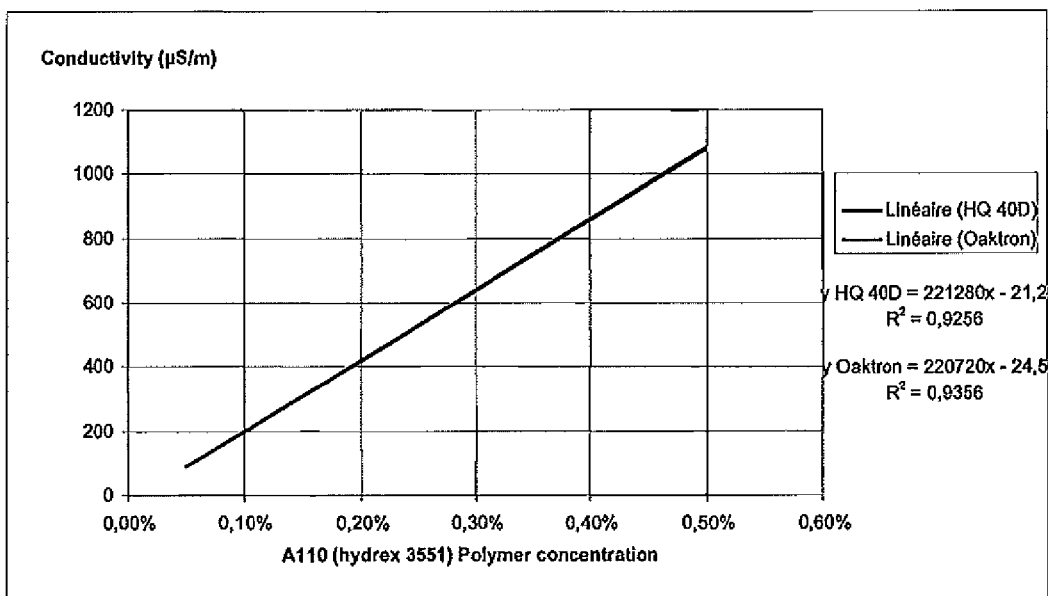
Figure 3:
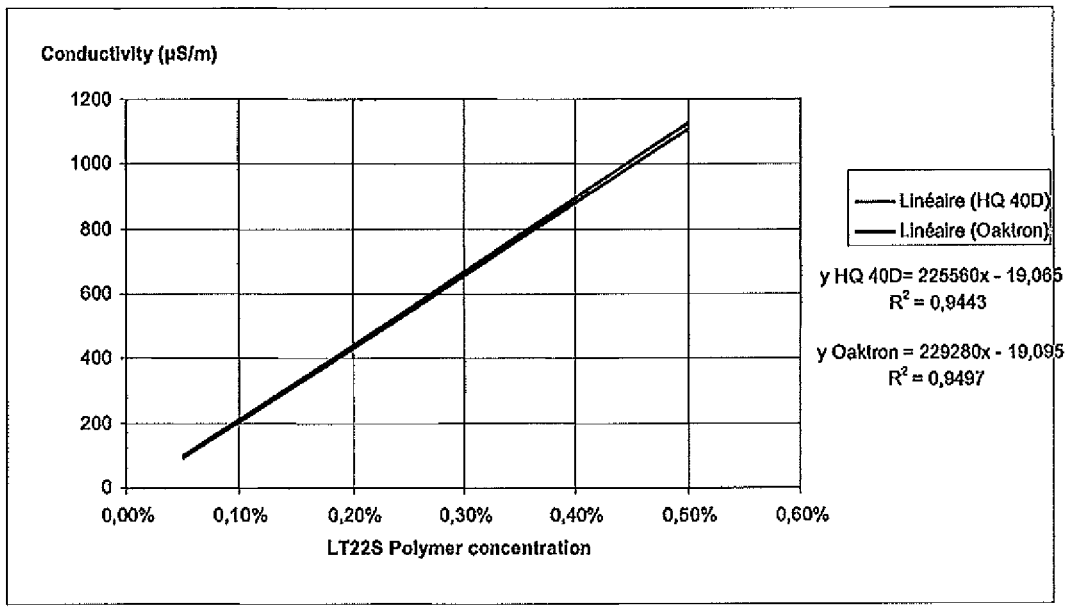
Figure 4:
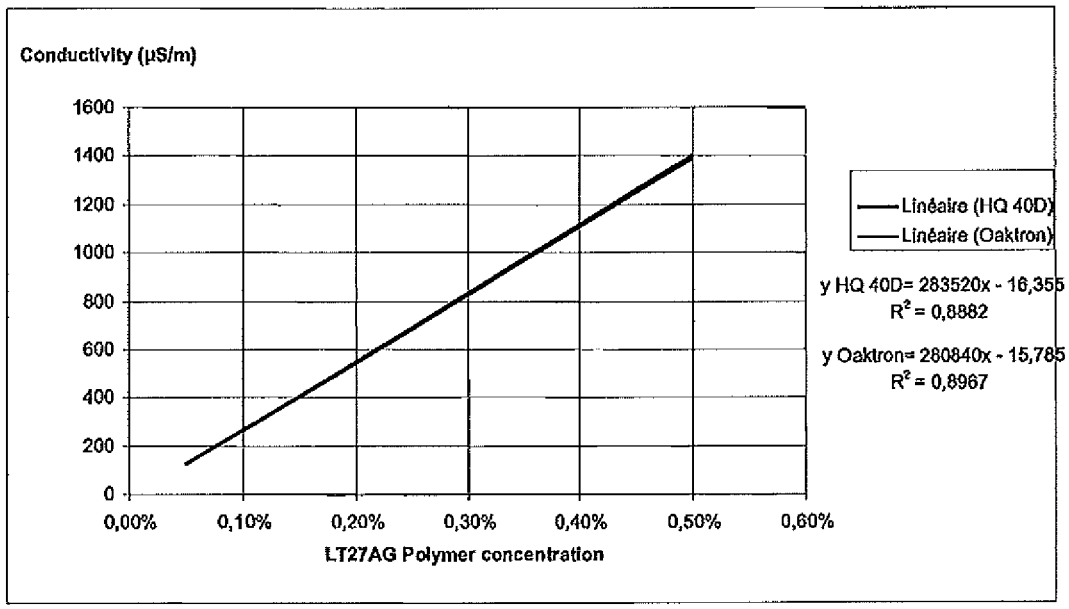
Figure 5:
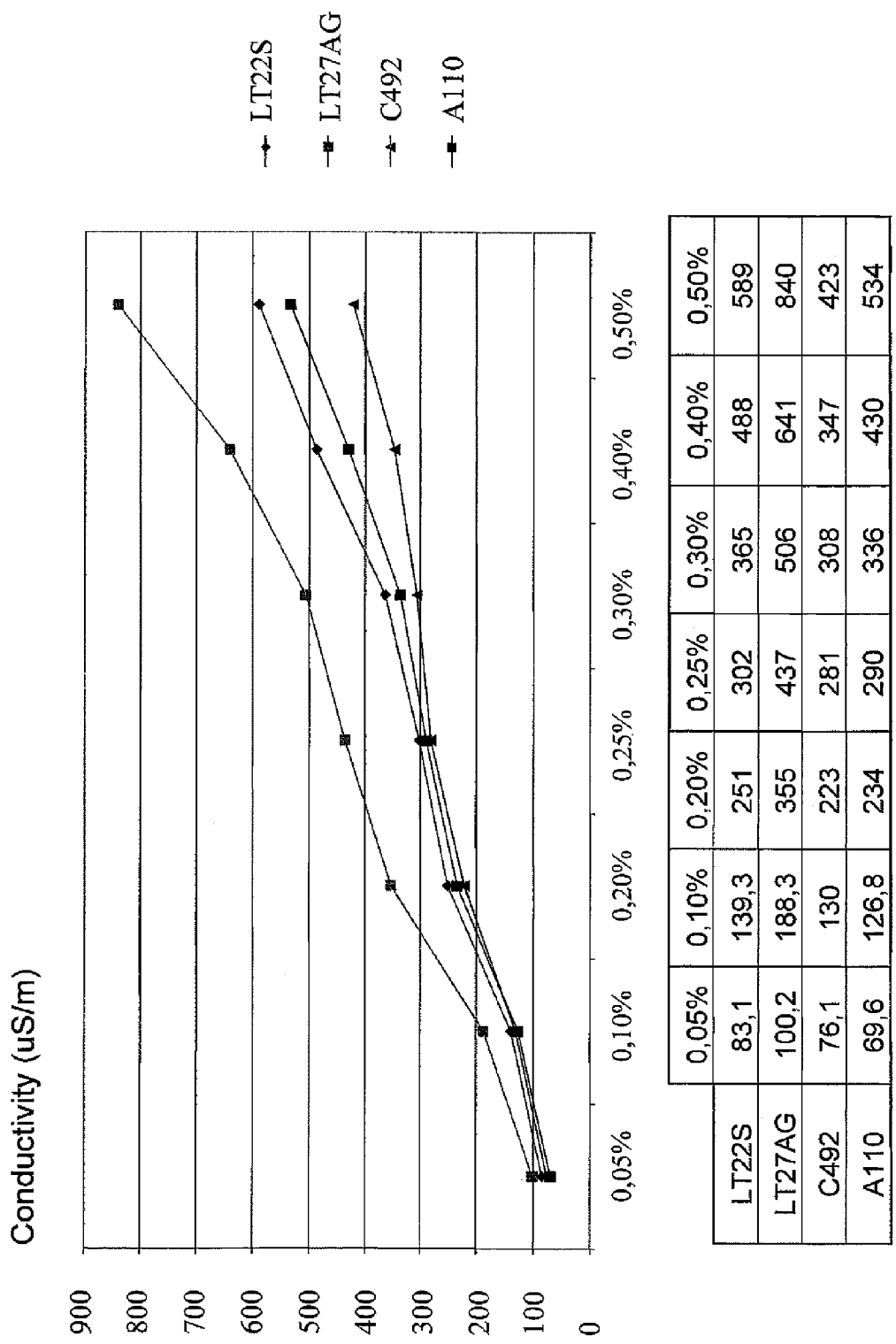
FIG. 5 is a graph showing the not perfectly but roughly linear relation between polymer concentration and conductivity measurement, between 0.05 and 0.50% in polymer concentration.

With respect to the curve of FIG. 5, the parameters were the same except that the measuring instrument was an Oakton Acorn. This curve suggests with more clarity that the conductivity variation with the concentration is not a perfectly linear relation. The curve ratio appears to vary depending on several factors, wherein the polymer chain formation is dependent on a variety of factors including:
  macromolecule size;
  concentration increase;
  duration of aqueous solution mixing;
  type of water used (i.e. degree of neutrality); and
  ionic dissociation (polyacrylamide being considered as high molecular weight polyelectrolyte).

Figure 6:
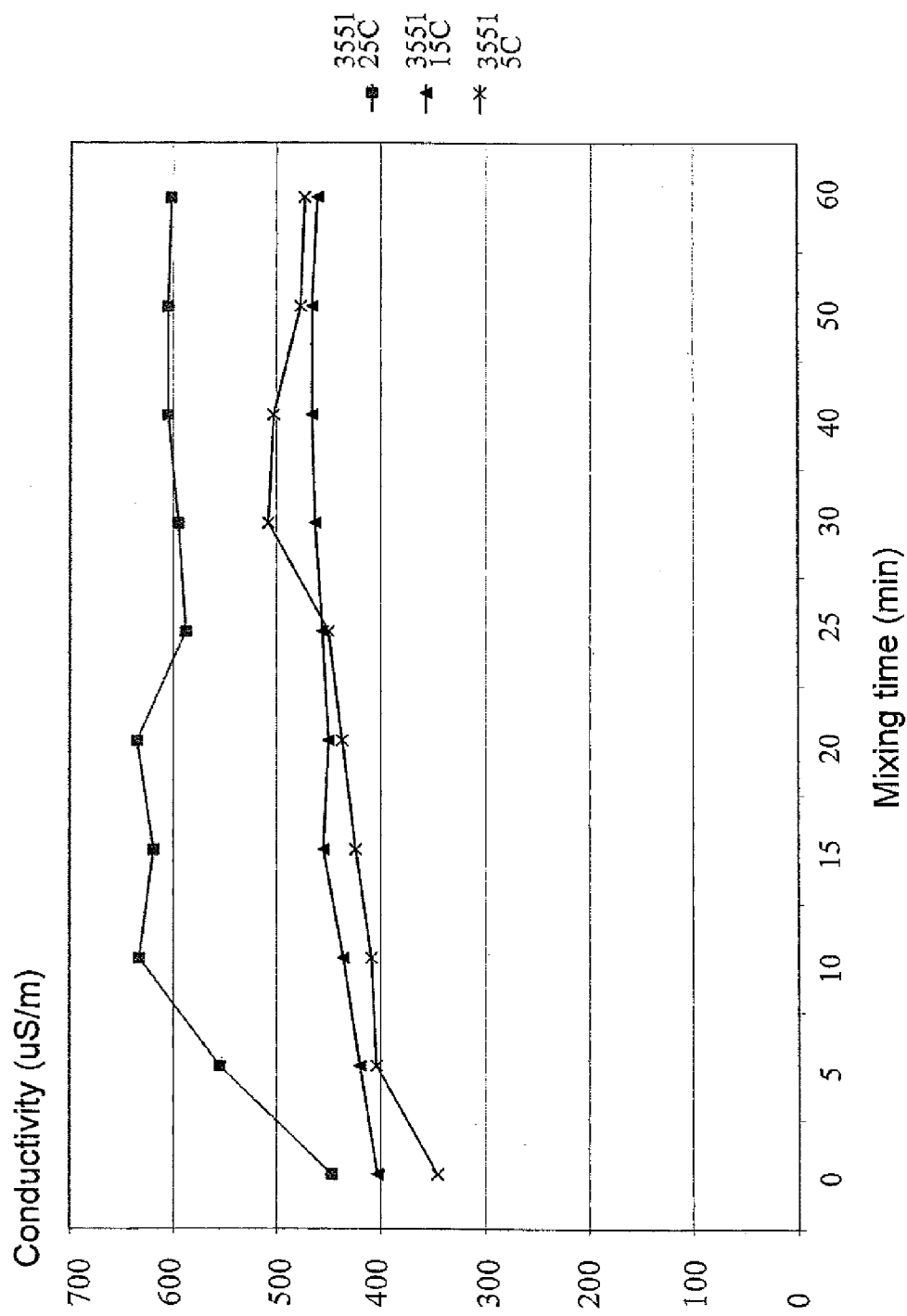
FIGS. 6 and 7 are graphs showing the impact aqueous solution mixing time on conductivity of various polymers inside the aqueous solution.
Figure 7:
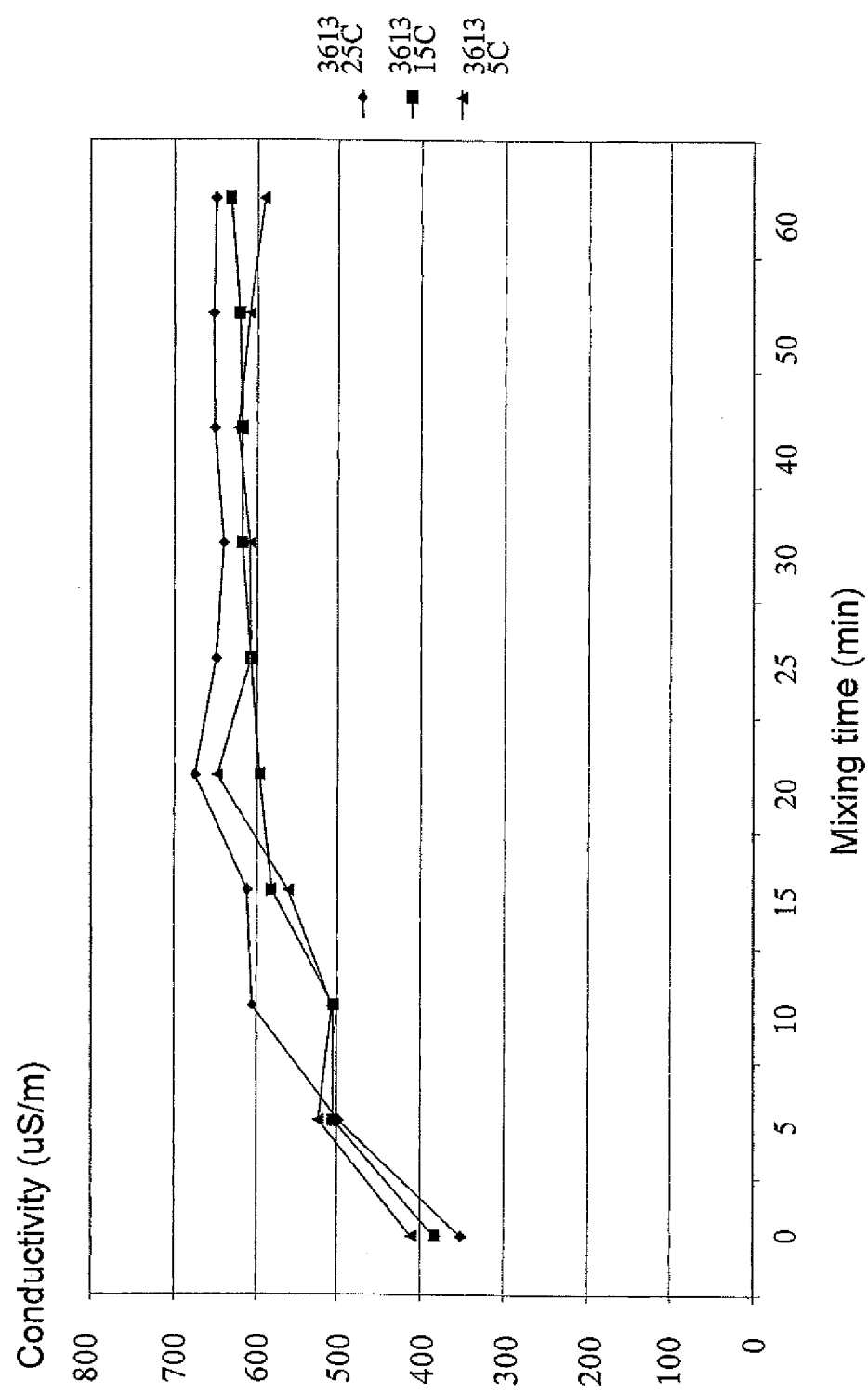
Figure 8:
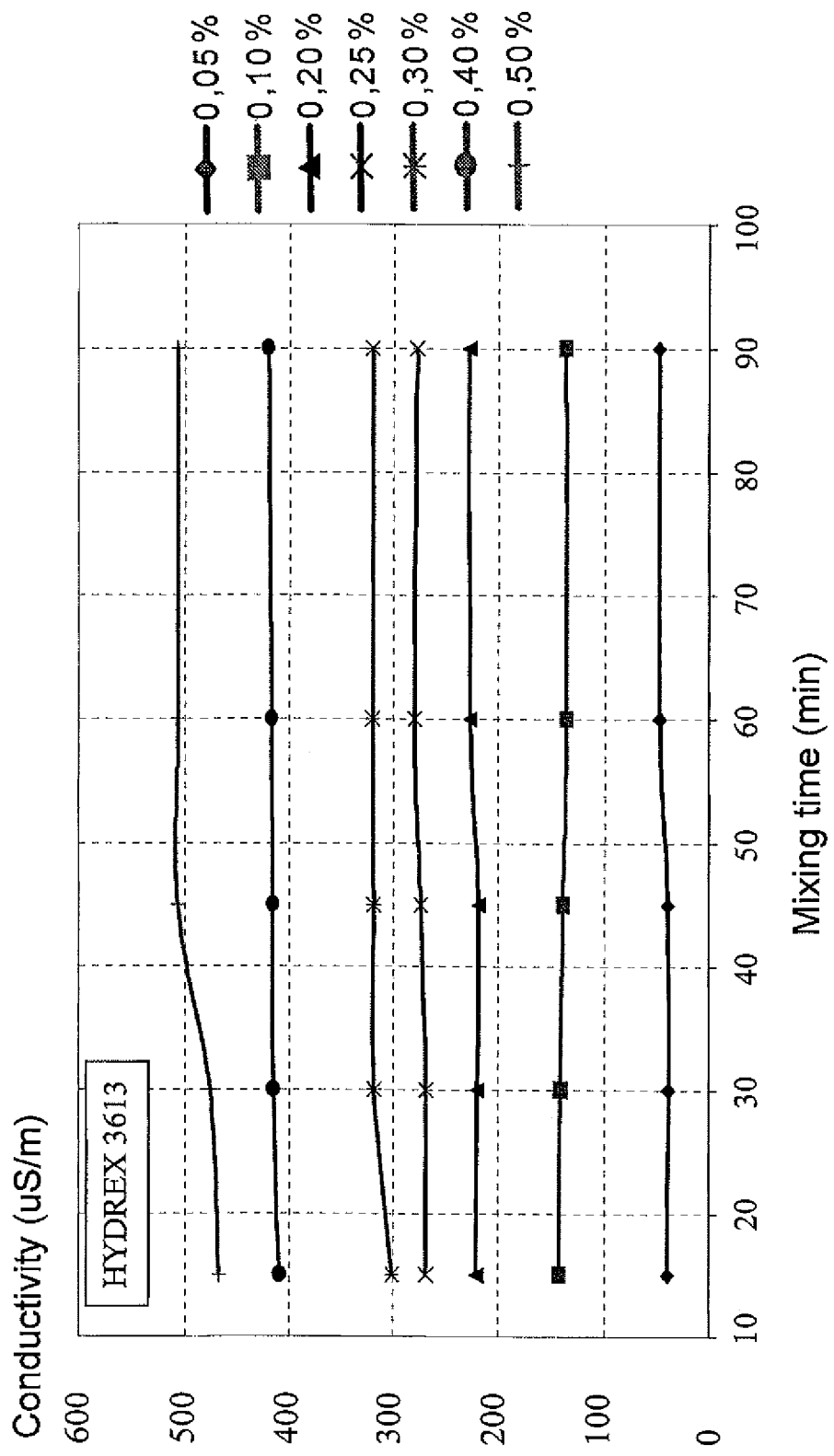
FIGS. 8 to 11 are graphs showing the generally linear relation between conductivity and polymer aqueous solution mixing time for various polymer concentration curves.
Figure 9:
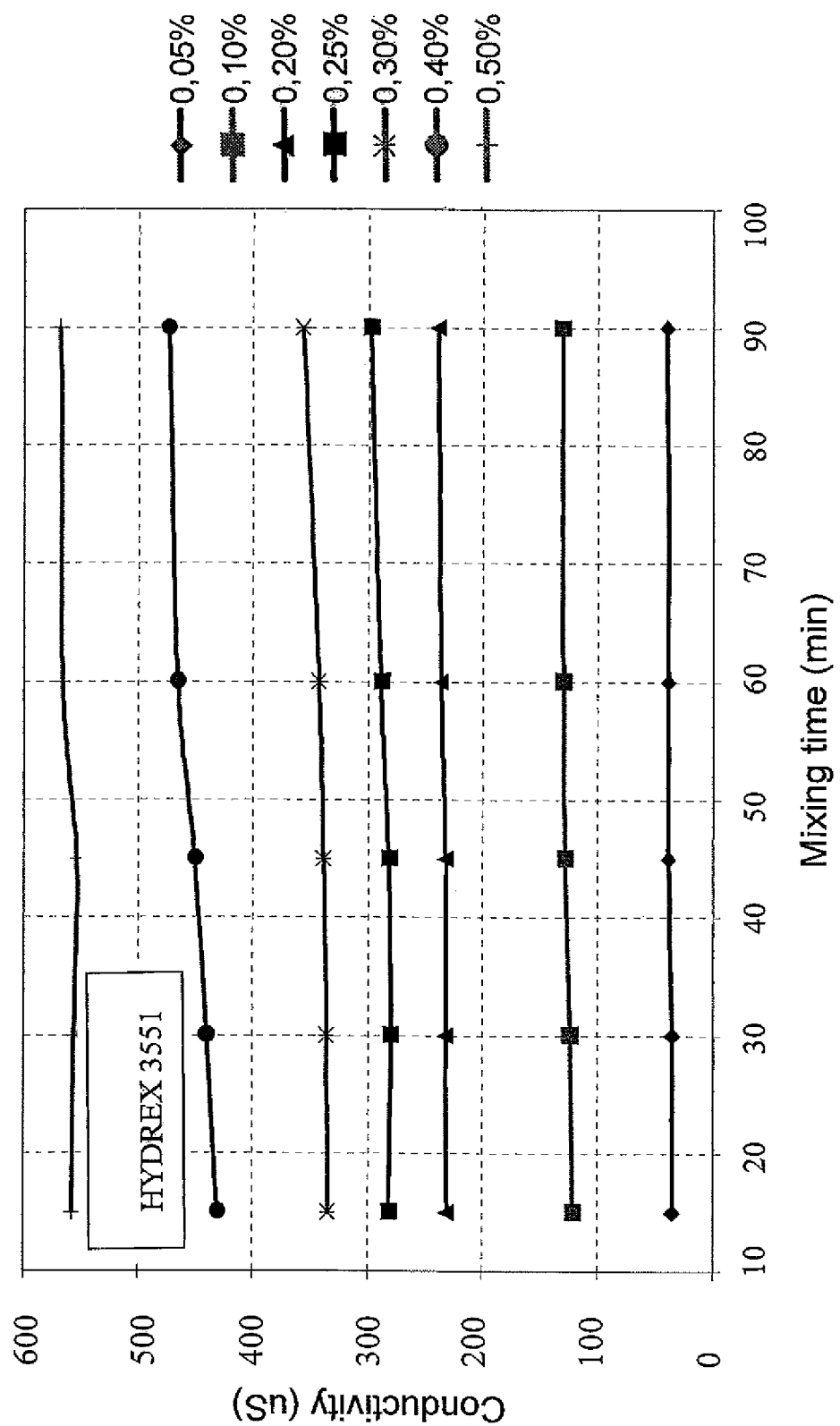
Figure 10:
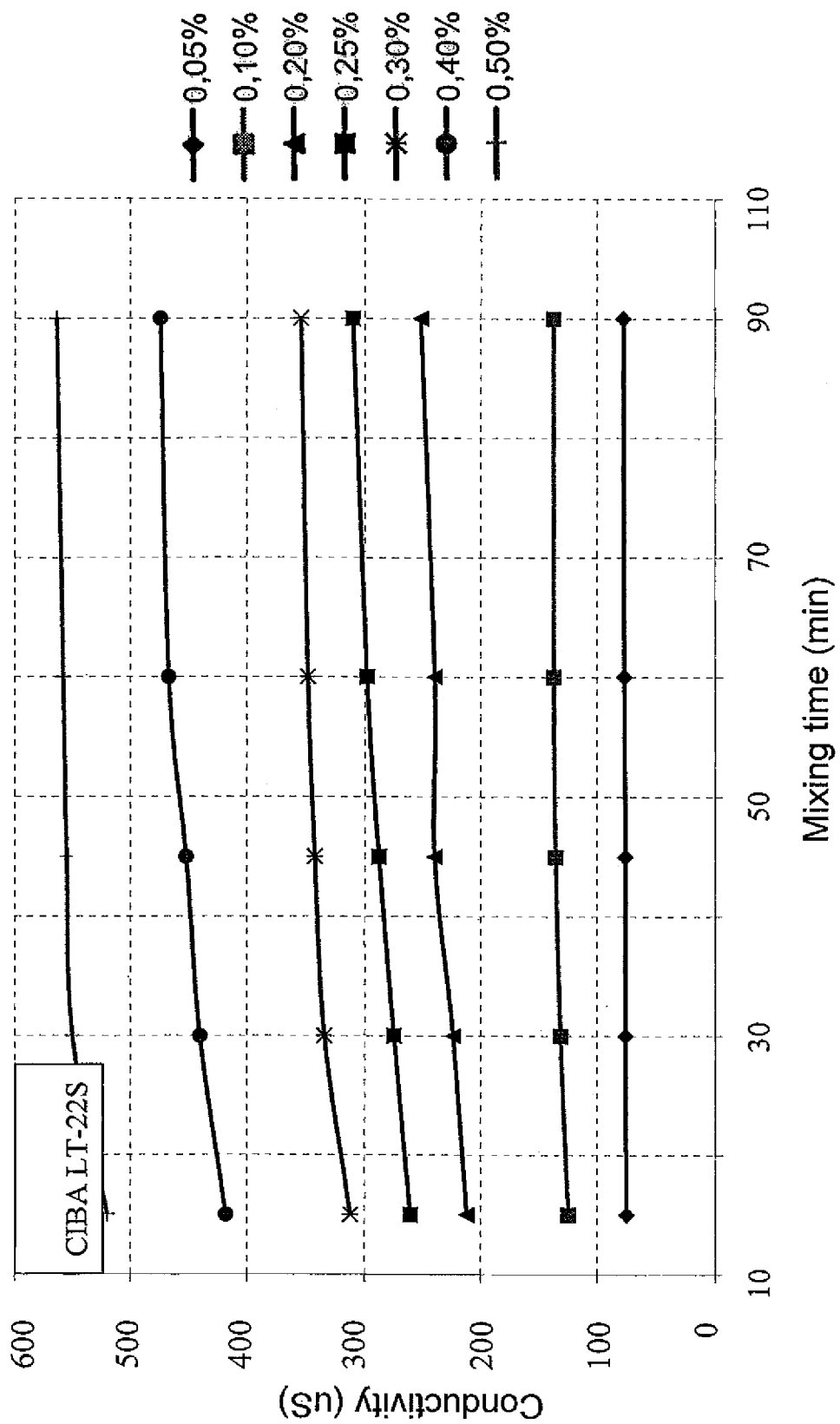
Figure 11:
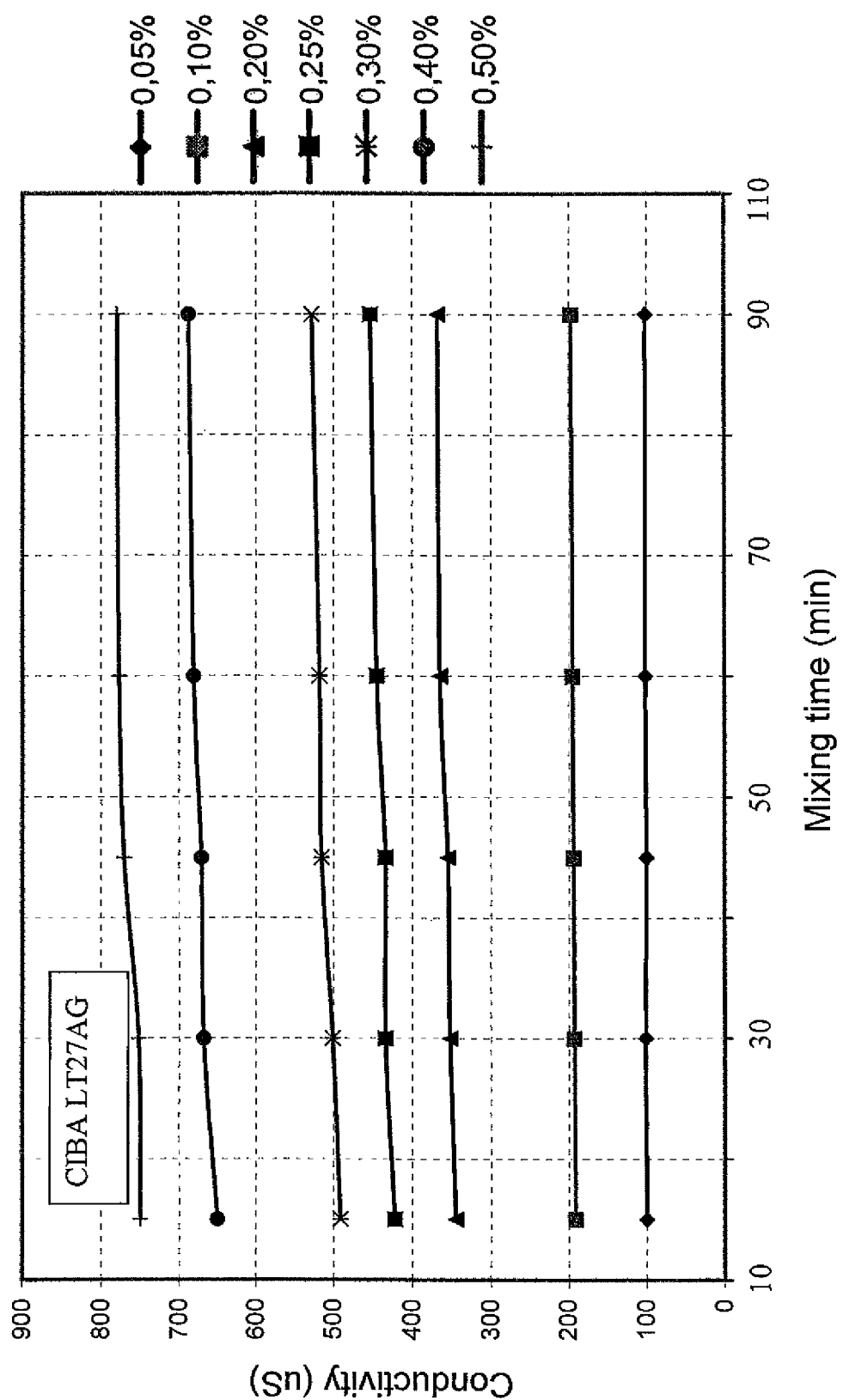
Figure 12:
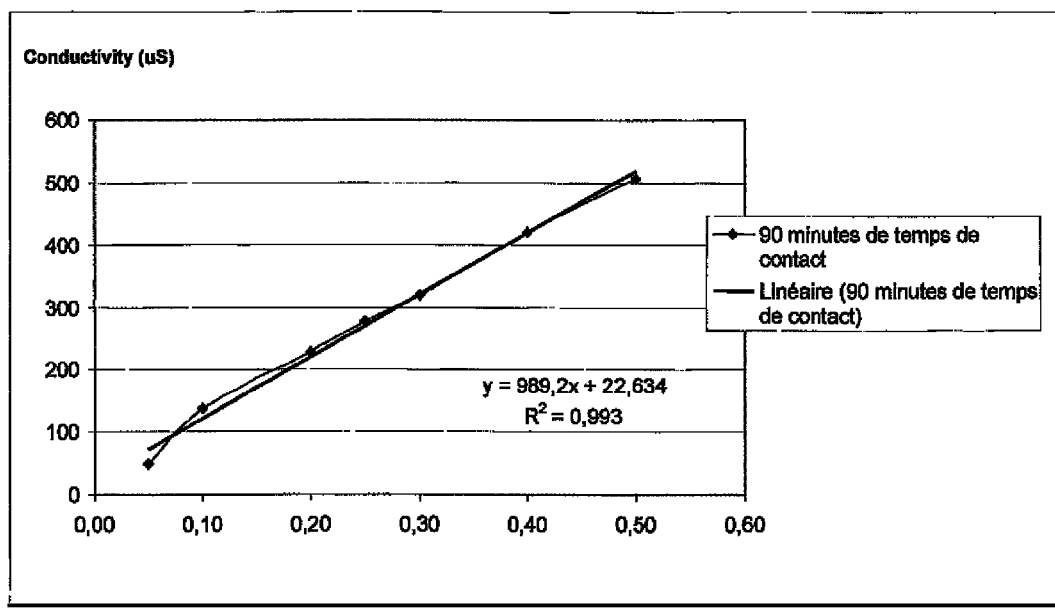
FIGS. 12 to 15 are graphs showing the generally linear relation between polymer concentration at 90 minutes mixing time relative to conductivity value, for four different polymers.
Figure 13:
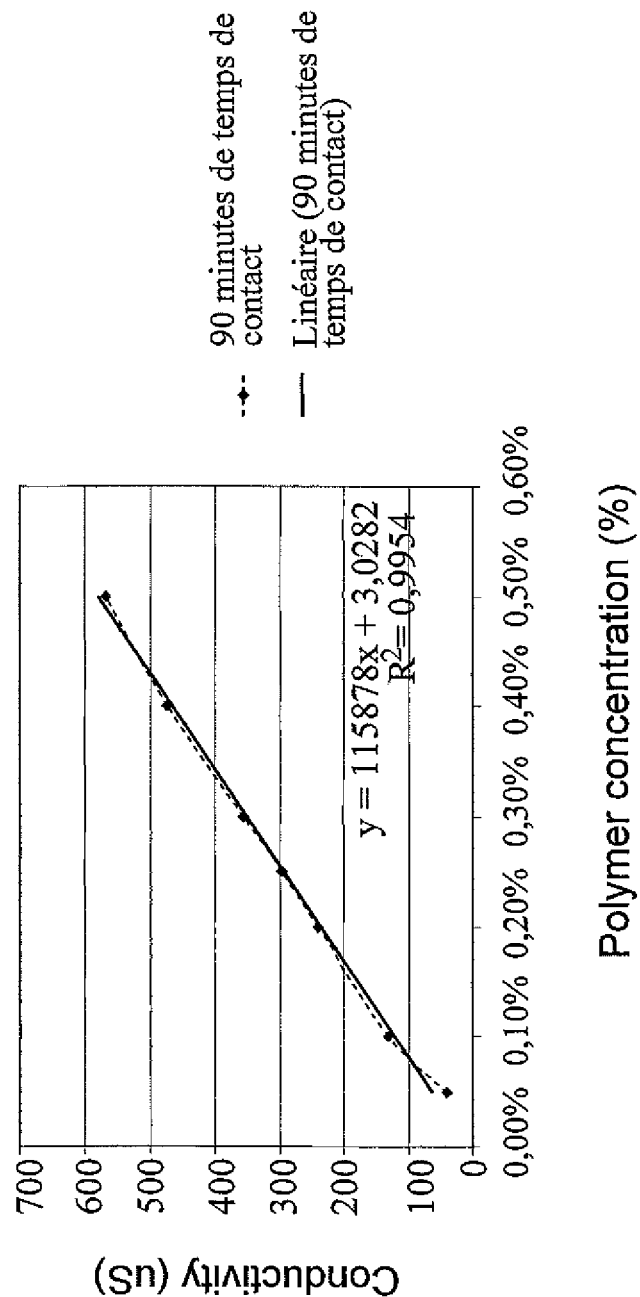
Figure 14:
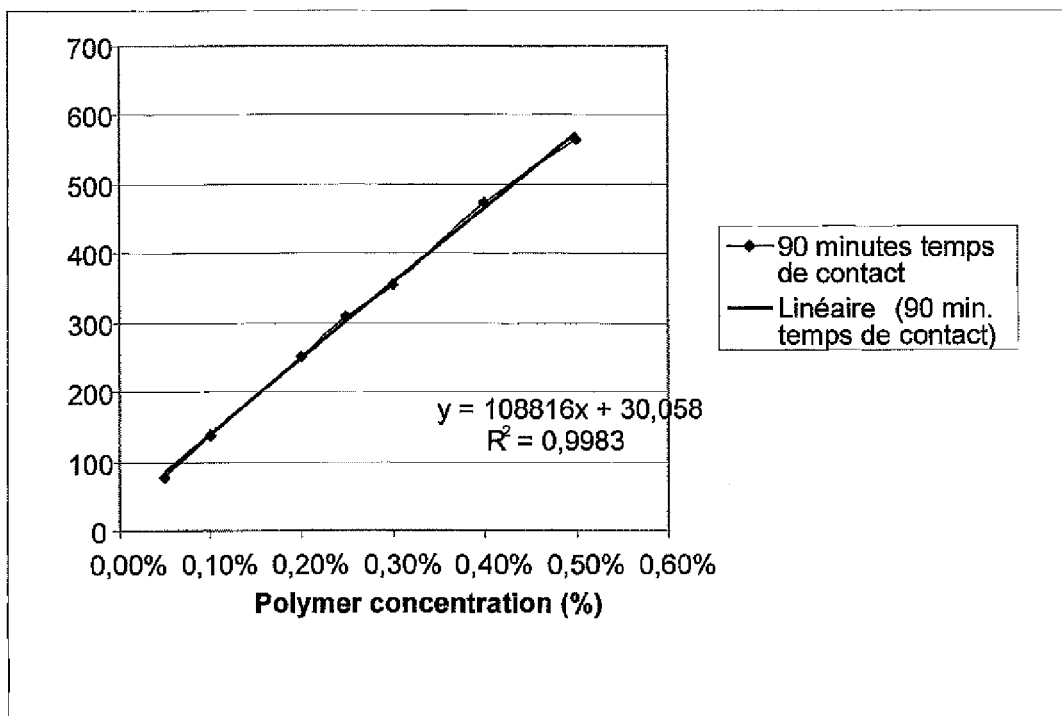
Figure 15:
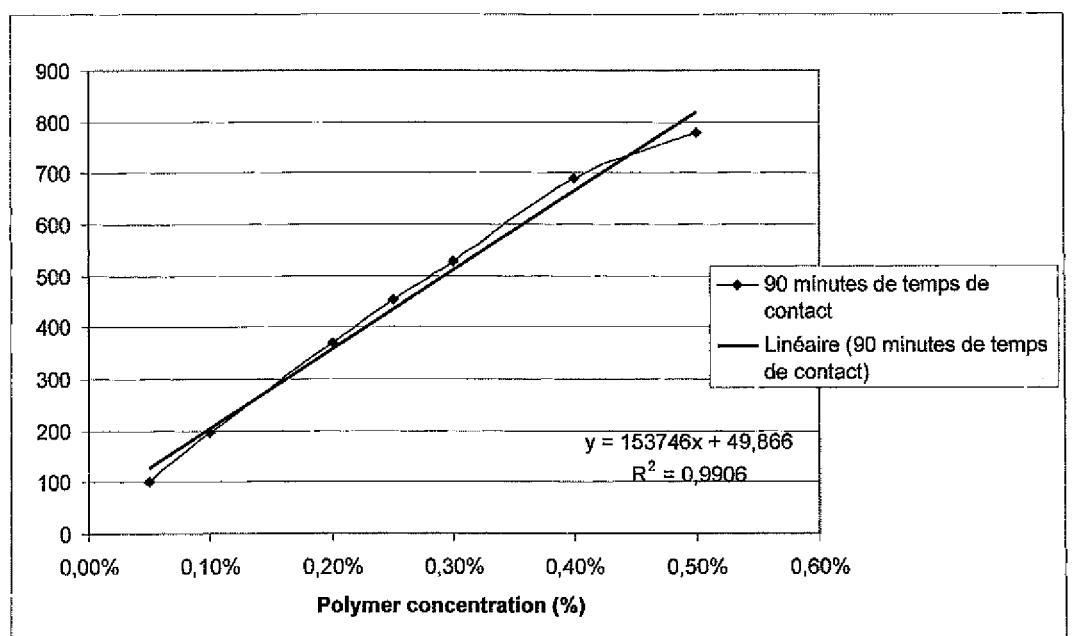

With respect to FIGS. 6 and 7, these tests were carried out in order to measure the effect of water temperature and maturing time. Tap water at 23.5 degrees Celsius was used, with polymer concentration of 0.25%. The tests show that water temperature has not a major effect on conductivity for the cationic polymer. However, it seems to have a bigger impact on anionic polymer. As all the curves seem to be quite similar to one another, the anionic curve may be wrong. Water temperature usually helps to dissolve polymer better in the pre-mixing stage and reduces polymer clogging in the system and excessive maintenance.

The polymer maturing time factor seems to be a more important factor as the curves seems to reach a plateau portion of the curves (where the curve has a lower ratio) after some time (roughly after 15 to 20 minutes for both cationic and anionic polymer). After that time, polymer was found (under visual inspection) to be well activated and appear appropriate to be used in this process. After 60 minutes, the polymer was found to be fully active (optimal activation) and completely ready to be used.

These graphs suggest that polymer activation could be related to conductivity increase. Conductivity is the ability to conduct an electrical current through a specific body. Therefore, as polymer chain formation increases, more ions become available, electric charge increases and conductivity increases. A fully activated polymer (for a certain concentration) under certain conditions could then be correlated by a conductivity plateau. This hypothesis seems to be correlated by all our tests as we are running relatively stable process conditions at very low concentrations. At high concentrations, on the other hand, this would probably not be the case as macromolecules size probably would be restrained by the high quantity of polymers and monomers available in the aqueous solution.

With respect to FIGS. 8 to 15, additional lab testing was conducted in order to demonstrate that polymers reach a top threshold conductivity value when fully activated. The tests in FIGS. 8 to 15 suggest the evolution of polymer conductivity depending on polymer concentration and maturing time.

After reaching the activation top conductivity value, i.e. a high conductivity level reached when polymer activation is nearly completed, the conductivity does not change with increased maturation (i.e. mixing) time. Therefore, when polymer activation is complete (i.e. in steady state), conductivity becomes stable. These graphs in FIGS. 8 to 15 clearly show the fact that aqueous solution conductivity measurement can be used to determine if polymer activation is complete. This measurement method can then be extended to compare different polymers; conductivity levels could be used to determine eventual activation capacity. It could also be used to develop special polymers with faster activation time, which could have an impact on full scale systems size or selection.

Additionally, FIGS. 12 to 15 show the evolution of the conductivity relative to the concentration and clearly indicate that the relation between conductivity and concentration becomes linear after polymer activation has become complete. Therefore, when polymer solution is fully activated and polymerisation reaction is completed, viscosity and conductivity reach their peak values and become stable over time. The Walden's rule can then be applied to this situation to express the relation between viscosity, concentration and conductivity.

In conclusion, it was found that conductivity measurement could be used to determine the polymer concentration in aqueous solution. Additionally, it was also found that conductivity measurement could also be used to represent the activation status of a conventional polyacrylamide typically used in a water treatment plant. Under certain conditions, there seems to be a linear relation between polymer concentration and aqueous electrical conductivity. This relation can only be valid when polymer become fully activated, i.e. when polymerisation is complete and polymer chains are fully formed.

Figure 16:
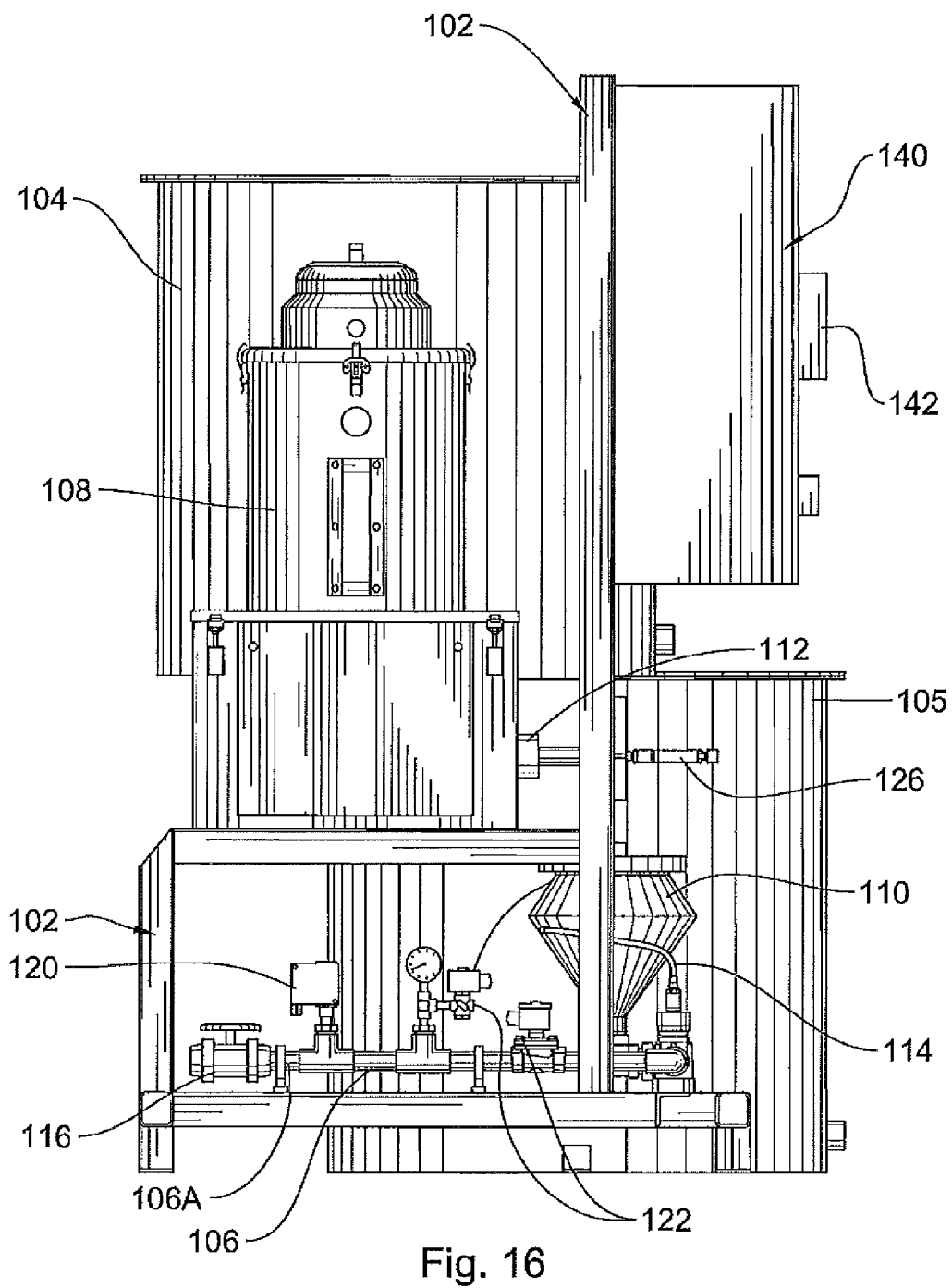
FIGS. 16 and 17 are elevational views from two different perspectives of the polymer make-up unit implementing the present method.
Figure 17:
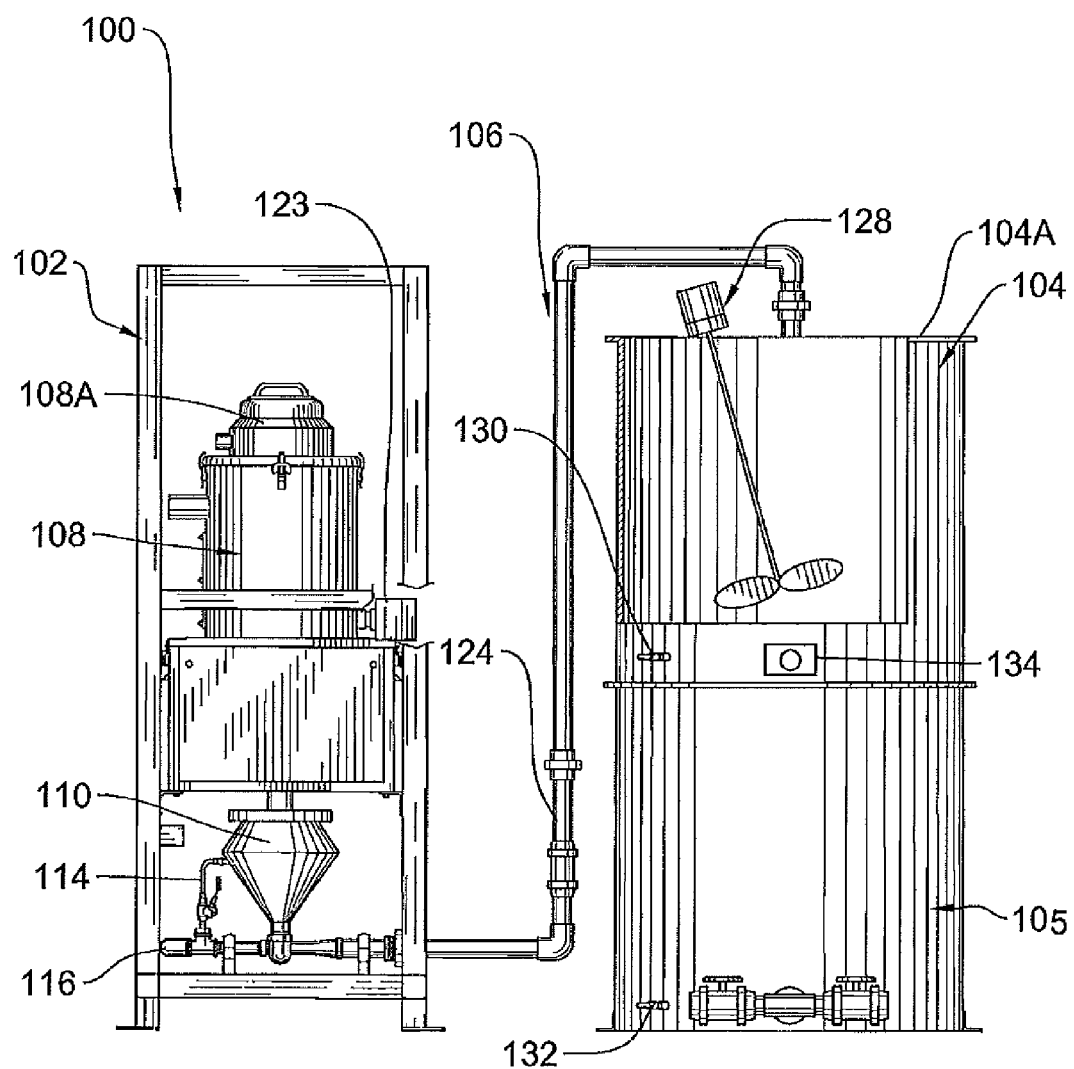
Figure 18:
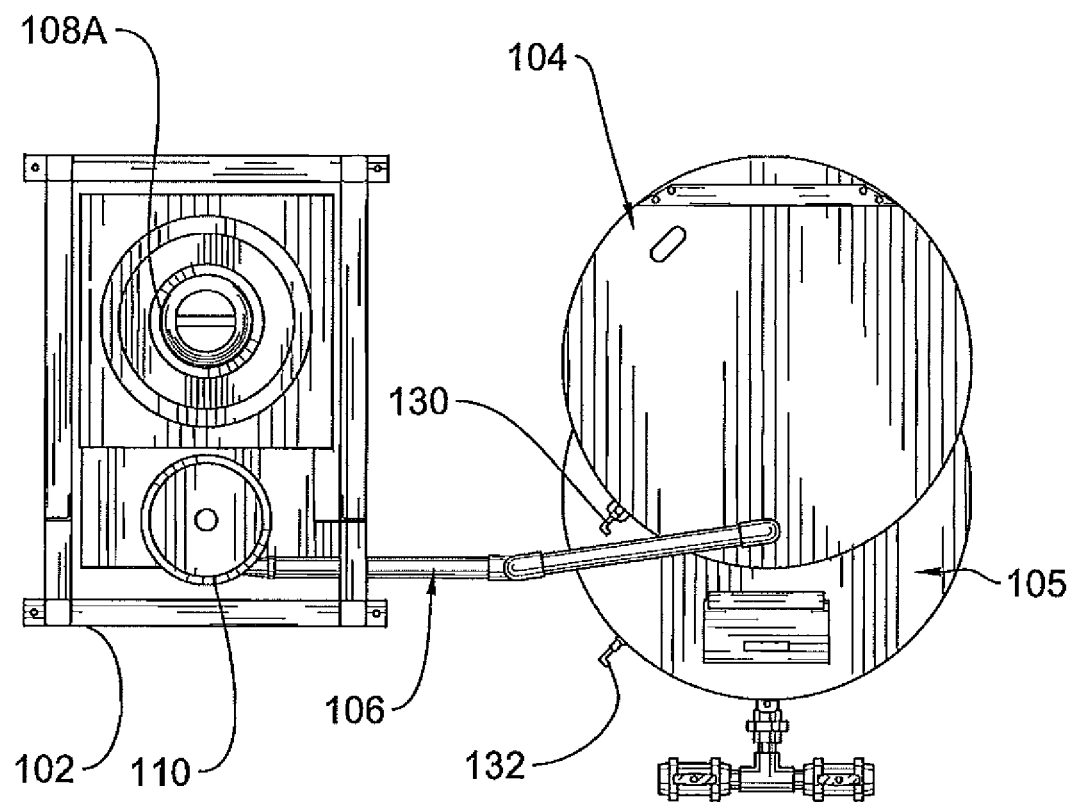
FIG. 18 is a top plan view of the polymer make up unit of FIG. 17.

It can now be shown in FIGS. 16 to 18 how the development and integration of a full scale conductivity measurement system can be implemented on a preferred embodiment of dry polymer makeup unit, 100. In order to confirm the findings from the laboratory tests, it was decided to install a conductivity meter 130 on a full scale polymer make-up system 100. The polymer make-up system 100 includes a dry feeder 108, dilution system with four intense wetting points, a mixing tank 104 where polymer maturation occurs and a storage tank 105 where water solution is pumped to the process.

More particularly, apparatus 100 includes a ground supported open frame 102, an upper water/polymer mixing tank 104 and a lower solution storage tank 105, both tanks 104, 105 spacedly standing from open frame 102, and an elbowed piping network 106 interconnecting the bottom portion of open frame 102 to the top end 104A of tank 104. A dry polymer powder hopper 108 is carried by frame 102 at an upper portion thereof, with a top vacuum loading station lid 108A for access to the dry polymer powder inside the enclosure thereof. A conical chamber 110 is also carried by frame 102 beneath hopper 108. Conical chamber 110 fluidingly interconnects hopper 108 and piping network 106, via an endless screw feeder 112 between hopper 108 and conical chamber 110, and via a flexible hose feeder 114 between piping 106 and conical chamber 110, wherein a polymer wetting cone system is obtained.

A water inlet means 116 (fed by a water source) is mounted to the upstream end 106A of piping 106, wherein conical chamber 110 is located intermediate piping upstream end 106A and mixing tank 104. Piping 106 is controlled by a low water pressure switch 120, solenoid valves 122, a low polymer level hopper sensor 123 and a turbulence generating deflector means 124. A hydraulic ram means with elastomeric valve, 126, is mounted to endless screw means 112 to form a feeder isolation valve, to prevent accidental backflow of water from conical chamber 110 to vacuum hopper 108. A water/polymer impellor agitator or the like mixing assembly 128 is operatively mounted into mixing tank 104. An intelligent control panel (CPU) assembly 140 into a control panel having a polymer activation status visualization screen 142 controls all components of apparatus 100.

Electrical conductivity probe 130 is mounted to the lower portion of water tank 104. A second conductivity probe 132 could also be mounted to water tank 105. A polymer/water solution discharge outlet valve 134 is provided at the lower portion of upper tank 104, for periodic discharge and economic retrieval of polymer/water solution.

In operation, low activation level dry polymer powder (e.g. between 1 and 3% activated) is fed under suction forces into vacuum hopper 108 through lid 108A. Water intake 116 is opened to feed water to upstream end 106A of piping network 106. Endless screw 112 is powered to deliver dry polymer powder from hopper 108 to conical wetting chamber 110. Pre-wetted polymer powder is then drawn into water piping 106 through hose 114 under venture forces. Polymer/water solution is brought to mixing tank 104 via piping 106, through top tank wall 104A. Mixing impellor agitator 128 is powered to thoroughly mix the polymer/water solution, during a period of maturation or mixing time sufficient as to maximize polymer activation status. Activated polymer/water solution is retrieved via discharge outlet 134, for economic reclaim.

The present polymer make-up system 100 is designed to prepare and activate dry polymers. Dry polymer is received in Super bags (typically 1,000 kg) or small bags (25 kg). The super bags are handled with an integrated motorized hoist and trolley. The super bag is supported by a structural frame. The small bags are handled with a vacuum loading station. The system can include a manual iris valve (to prevent dusting during bag change-out), storage hopper 108, hopper empty level switch 123 and other accessories required for safe operation of the system.

Dry polymer is fed into the wetting system via a Hapman Posiportion™ volumetric feeder 112. The volumetric feeder includes an agitated flexible hopper. The hopper is kept in movement by two mechanically actuated paddles. This system prevents polymer bridging and provides very high powder metering accuracy. The feeder discharge spout incorporates an air inlet to allow for moisture escape. The feeder is closed by a spring-loaded hydro-mechanical gate 126 to prevent moisture contact with dry polymer.

In order to effectively activate the polymer particles, the system must include a high energy pre-wetting stage to start the polymer inversion reaction. When all polymer particles are pre-wetted, the solution must be exposed to low-shear agitation in order for the polymer chains to be completely activated. The wetting system is composed of four (4) different wetting/contacting elements. The pre-wetting high shear stage takes place in a non-mechanical wetting chamber 114. Polymer particles come in contact with high-speed water in the stainless steel wetting cone. The pre-wetted polymer particles will then be transported via a high-energy, stainless steel eductor where another pre-wetting stage will be achieved. The solution will then be transported to the mixing tank 104 via transport pipe 106. The transport pipe 106 will integrate a static mixer 124 to optimize polymer wetting before entering into the mixing tank 104.

The mixing tank 104 will include low-shear agitator 128. Agitator speed will preferably be limited to 180 rpm and impeller size will be selected for optimal mixing geometry and power consumption (approx. 0.33 D/T ratio, where D is the impeller diameter and T is the tank diameter). Mixing tank 104 and storage tank 105 will be constructed from 304 SS, 2b finish. Mixing and storage tanks will be cylindrical in order to eliminate mixing dead zones. Tank level monitoring will be done through pressure transmitters (4-20 mA signal) or level floats.

Mixing and storage tanks 104, 105, are equipped with conductivity process probes 130, 132. Mixing tank probe 130 is used to provide real-time polymer activation curve and status. Storage tank probe 132 is used to provide activation confirmation and polymer quality confirmation.

All operations are completely automated through local control panels suited with CPU 140. Control panels are built and tested to the customer's specifications and integrate polymer conductivity probe analysers and polymer activation CPU unit for information treatment.

The two conductivity meters 130, 132, used for the trial tests are preferably a portable Oakton Acorn meter 130 and a Hach D3422GB3 process conductivity analyser 132. The portable conductivity meter 130 allows us to follow polymer activation (conductivity levels) in the mixing tank 104. The process conductivity analyser 132 was installed in the storage tank 105 to follow conductivity level of finished fully activated polymer. This measure can give us an indication of the activation status and/or the concentration status. During the trial test, the conductivity meter 130 was used to follow the activation status of the polymer in the mixing tank 104. It was found that conductivity was increasing very fast in the first minutes of reaction to reach a plateau value when activation was completed and viscosity was at its maximum. Additionally, the conductivity probe 132 installed in the storage tank 105 (where polymer can only be transferred if fully activated) demonstrates that polymer conductivity could be followed easily and correlated to polymer concentration and activation with acceptable accuracy and repeatability. The full scale application was found to confirm the lab trials.

We found that the conductivity is instrument relative (difference of 20 to 30 micro Siemens on all tests). We also found that conductivity meter 132 may be installed in the storage tank 105 if the goal is to confirm concentration or activation. It could be installed in the mixing tank 104 if the goal is to validate polymer activation, activation curve or polymer reaction.

The full scale measurement system includes three (3) steps:
1. on site trials with fixed conductivity meter 130,132, and end-user water (to calibrate the meter with the real process water as conductivity is site-related) and data entering in control system;
2. measurement readings in storage tank 105; and
3. automated comparison between actual on-line readings and on-site trial values (pre-set in control system). Alarm is raised if difference is important.

The measurement system when integrated in a full scale automatic dry polymer make-up system 100, provides the operator with an indication that the solution conductivity is out of expected range and therefore that concentration or activation may not be optimal. Additionally, the system reduces the risks of decreasing the efficiency of the flocculation, filtration or thickening process.

In conclusion, the developed method has been found to be a valid measurement method to determine polymer concentration or activation. The laboratory tests and the full scale tests confirm our hypothesis. The conductivity meter 130 (132) has been found to be a good instrument to validate polymer activation and polymer concentration. The system should be calibrated on-site, with the real water and the real polymer to offer accurate information to the end-user. Potential applications include:

the system has been developed to provide a valid and inexpensive method to confirm polymer concentration and activation in aqueous solution;
the system could also be used to compare and select polymers in a specific applications;
if the conductivity measurement is an indication of the electrical charge, the measurement method could possibly help to reduce process treatment footprint, if better polymer is used, but further testing would be required to verify same.

The embodiments of the invention, in which an exclusive property or privilege is claimed, are defined as follows:

1. A method of measuring activation status of a water treatment polymer in an aqueous solution and of expressing concentration thereof, the method comprising the following steps:
   supplying low activation level polymer to water to form an aqueous solution;
   providing a verification system for polymer activation of said polymer;
   calibrating said verification system;
   generating an activation target value associated with the preceding calibration step;
   monitoring electrical conductivity in the aqueous solution with said verification system;
   correlating said conductivity against elapsed time with polymer concentration to determine a polymer activation status in the aqueous solution; and
   mixing the aqueous solution for a period of maturation time sufficient to enable substantially complete activation of the polymer, when conductivity achieves steady state and reaches said target value.

2. A method as in claim 1, further including a further last step of suspending said maturing time, once conductivity achieves a steady state associated with complete activation of the aqueous sample polymer.

3. A method as in claim 2, further including a further last step of display of progression of activation level of said aqueous solution polymer, enabling real time monitoring visualization thereof by an operator for confirmation of quality of said aqueous solution.

4. A method as in claim 3, wherein the water treatment polymer is selected from the group comprising weak electrolytes with high molecular weight.

5. A method as in claim 4, wherein the water treatment polymer is selected from the group comprising anionic and cationic type polymers.

6. A method as in claim 1, wherein said step of supplying polymer to water to from an aqueous solution, is performed in a continuous fashion.

7. A method as in claim 1, wherein said step of supplying polymer to water to form an aqueous solution, is performed in a batch mode.

8. A method of optimizing polymer make-up performance, comprising the following steps:
   a) feeding water to a polymer make-up unit water tank;
   b) diluting low activation level polymer into the water tank, wherein a polymer/water-solution is formed inside the tank;
   c) monitoring electrical conductivity of said solution;
   d) correlating said conductivity with polymer concentration to determine a polymer activation status; and
   e) once said conductivity achieves a steady state plateau, suspending feeding of said activated polymer.

9. A method as in claim 8, further including a step of mixing of said solution inside the tank, between steps b) and c), wherein maturing time of said aqueous solution mixing is sufficient to enable complete activation of the polymer in said solution.

10. A method as in claim 9, wherein the polymer is selected from the group comprising anionic and cationic type polymers.

11. A method as in claim 8, wherein said step of supplying polymer to water to form an aqueous solution, is performed in a continuous fashion.

12. A method as in claim 8, wherein said step of supplying polymer to water to form an aqueous solution, is performed in a batch mode.

13. A polymer make-up unit comprising:
   a water tank enclosing an aqueous solution;
   a polymer feeding system feeding polymer to said water tank;
   low activation level polymer being supplied and thoroughly mixed in the aqueous solution inside said water tank;
   a CPU;
   a conductivity meter probe sensitive to electrical conductivity in the aqueous solution;
   said conductivity meter probe and CPU being operatively interconnected wherein said CPU continuously monitors conductivity and correlates against elapsed time said conductivity with polymer concentration to determine a polymer activation status;
   wherein performance of said water treatment unit is optimized.

14. A polymer make-up unit as in claim 13, further including a display means accessible by an operator of the make-up unit and operatively connected to said meter probe conductivity and CPU, wherein real time visualization by an operator of concentration and expression of activation status of the polymer in the aqueous solution is enabled.

15. A polymer make-up unit as in claim 14, wherein the water treatment polymer is selected from the group comprising anionic and cationic type polymers.

16. A make-up unit as in claim 13, wherein said polymer is continuously supplied in the aqueous solution inside said tank.

17. A make-up unit as in claim 13, wherein said polymer is intermittently supplied in the aqueous solution inside said tank.

* * * * *